United States Patent [19]

McCoy et al.

[11] Patent Number: 5,064,943
[45] Date of Patent: Nov. 12, 1991

[54] METHOD FOR SOLUBILIZATION AND NATURATION OF SOMATOTROPIN

[75] Inventors: Kevin M. McCoy, Hudson, N.J.; Robert A. Frost, Westchester, N.Y.

[73] Assignee: American Cyanamid Company, Stamford, Conn.

[21] Appl. No.: 285,477

[22] Filed: Dec. 16, 1988

[51] Int. Cl.$^5$ .................. C07K 3/12; C07K 15/06
[52] U.S. Cl. .................. 530/399; 435/69.4; 530/412
[58] Field of Search .............. 530/399, 350, 412; 435/69.4

[56] References Cited

U.S. PATENT DOCUMENTS

| 4,511,503 | 4/1985 | Olson et al. | 530/422 |
| 4,652,630 | 3/1987 | Bentle et al. | 530/344 |
| 4,677,196 | 6/1987 | Rausch et al. | 530/412 |

FOREIGN PATENT DOCUMENTS 0122080 10/1984 European Pat. Off.
WO83/04418 12/1983 PCT Int'l Appl.

OTHER PUBLICATIONS

Sharma, S. K., 1986, Separation Science and Technology 21(8):701-726.

Primary Examiner—Garnette D. Draper
Assistant Examiner—Keith C. Furman
Attorney, Agent, or Firm—Estelle J. Tsevdos

[57] ABSTRACT

A method for solubilization and naturation of somatotropin using an aqueous alkaline solution results in lower dimer formation and eliminates denaturants and separate renaturation steps and agents.

7 Claims, 7 Drawing Sheets

METHOD FOR SOLUBILIZATION AND NATURATION OF SOMATOTROPIN

BACKGROUND OF THE INVENTION

In recent years recombinant DNA technology has made possible the large scale production of proteins. Several methods for the solubilization and naturation of somatotropin protein have been the subject of U.S. Patents. For example U.S. Pat. No. 4,511,503 discloses a typical scheme for recovering proteins from refractile bodies. Refractile bodies are insoluble granules of aggregated denatured somatotropin located in the cytoplasm of the *Escherichia coli* (*E. coli*) cell which are visible as bright spots under a phase contrast microscope. The refractile bodies are caused by the over production of somatotropin as a result of genetic manipulation of the *E. coli* plasmid DNA. The refractile bodies are often treated with a strong denaturant or chaotropic agent which causes the improperly folded molecules to unfold and become soluble. The protein must then be "renatured." Properly natured monomeric somatotropin is the goal. The refractile bodies cannot be used without this unfolding and refolding because they are biologically inactive in the refractile state. The most commonly employed strong denaturant in schemes of this type has been guanidine hydrochloride.

Other methods have involved other chaotropic agents such as sodium dodecyl sulphate (SDS) (e.g. U.S. Pat. No. 4,677,196), or weak denaturants such as urea (e.g. U.S. Pat. No. 4,731,440).

Each of the methods of solubilization and naturation of somatotropin have had problems. Guanidine hydrochloride is very expensive and must be replaced for the naturation process to occur. SDS is a highly effective denaturant and much less expensive than guanidine hydrochloride, but SDS binds to the denatured protein much more tightly making its complete removal from the protein problematic and concurrently increasing processing costs. Urea is usually used as a weaker denaturant or chaotropic agent. But even methods using urea have had problems such as contamination of the final product and handling, storage and waste treatment problems.

In addition to the other problems of conventional methods, properly natured monomer is not the only product. Somatotropin monomer is the smallest unit of protein that still retains all of the properties and biological activity of somatotropin. Typically somatotropin monomer consists of approximately 191 amino acid residues and has a molecular weight of roughly 22,000 daltons. The monomeric molecule is neither covalently linked to nor non-covalently associated with other similar molecules.

Somatotropin dimer consists of two monomer molecules which are either covalently linked, e.g. through intermolecular disulfide bonds, or non-covalently associated with one another. The dimer molecule consists of double the number of amino acid residues and double the molecular weight of a monomeric molecule.

Unfortunately employing conventional methods, some dimer is formed, as well as higher molecular weight protein molecules. Only the monomer and not the dimer is biologically useful.

Therefore what is needed in the art is a commercially feasible method for the solubilization and naturation of somatotropin which produces good yield of monomer, without excess dimer and without the use of chaotropic agents.

SUMMARY OF THE INVENTION

A method for solubilization and naturation of somatotropin without the use of chaotropic agents and the monomeric somatotropin produced by the method are disclosed. The method comprises dispersing somatotropin refractile bodies into water to form a suitable concentration, adjusting the pH to a range from about pH 11.5 to about pH 12.5, maintaining the pH range for sufficient time to completely solubilize the refractile bodies, optionally readjusting the pH of the solution to a range from about pH 11 to about pH 12, maintaining the solution at the readjusted pH range, resulting in somatotropin content composed of properly natured monomeric somatotropin in good yield.

Surprisingly, the present invention results in lower dimer formation and eliminates the need for any separate "renaturation" step(s) or agents.

DETAILED DESCRIPTION OF THE INVENTION

The present invention is directed to a method for solubilization and naturation of somatotropin which comprises: dispersing somatotropin refractile bodies into water in a suitable concentration; adjusting the pH of the refractile bodies in water to a level to effect solubilization; maintaining the pH for sufficient time to solubilize the refractile bodies; optionally readjusting the pH of the solution to a level to effect naturation; and maintaining the solution at the readjusted pH for a time sufficient to result in the somatotropin content in solution to be composed of properly natured monomeric somatotropin in good yield.

"Somatotropin" as used herein denotes (1) animal growth hormone, derivatives, analogs and fragments thereof of whatever species, for example, human, bovine, or porcine; (2) precursors to growth insulin, such as reduced (—SH) growth hormone and S-protected growth hormone, for example, growth hormone S-sulfonate; (3) variants of growth hormone or its precursors, for example, structures which have been modified to lengthen and/or shorten the growth hormone amino acid sequence, for example the 20K variant of human growth hormone, methionyl human growth hormone, Δ7 and Δ9 porcine growth hormone and the like; and (4) analogs of growth hormone or its precursors, for example structures in which the growth hormone amino acid sequence has been modified by replacement of one or more amino acid residues. Both recombinantly derived somatotropin and naturally occurring somatotropin as well as any other type of somatotropin may be utilized in accordance with the present invention.

Figure 1:
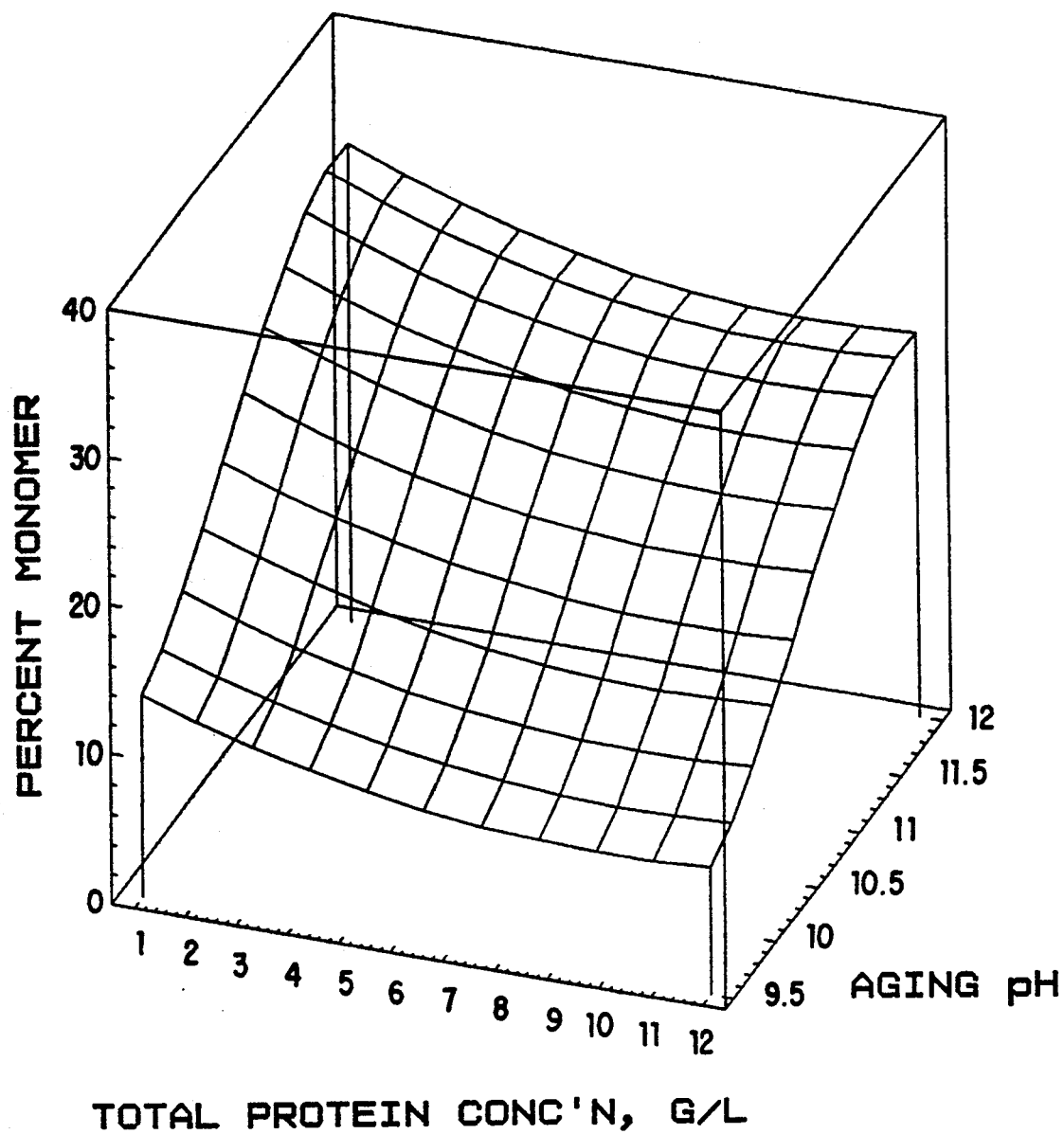
FIG. 1 diagramatically represents yield of monomer as dependent upon aging pH and concentration of protein.

The first step in the novel method is the dispersal of the somatotropin refractile bodies into water (preferably deionized water) at a suitable concentration. Concentration of total protein is an important factor of the present invention. As FIG. 1 shows the yield of monomer depends upon the total concentration of the protein. A suitable concentration is less than about 5.0 g/l and preferably in the range of 0.5 g/l to about 5.0 g/l. Especially preferred is a concentration of about 2.5 g/l. As concentration increases beyond about 5.0 g/l range the process results tend to suffer. Even though solutions at concentrations below about 0.5 g/l appear to have better results in terms of percent yield of monomer, commercial factors such as storage, capital cost and size of equipment as well as the additional steps further in the process to remove the excess liquid, do not favor using such a dilute solution.

The pH of the concentrated somatotropin is adjusted to a range from about pH 11.5 to about pH 12.5, preferably about pH 12.0 to about pH 12.2 to solubilize the somatotropin in the water. Any strong base may be used to adjust the pH of the solution (e.g. the addition of sodium hydroxide or potassium hydroxide). This solubilization generally takes place in a relatively short period of time, about two to twenty minutes is typical. With the pH at this range the refractile bodies visibly are dissolved and the solution clears. After the somatotropin refractile bodies are dissolved, the pH may be maintained or lowered. If maintained the somatotropin gradually folds and yields properly natured monomer. No "renaturing" steps are required because no denaturant is used. Instead the alkaline environment provides solubilization in a naturing type of environment. A naturing environment refers to the set of physical and solvent conditions which allow somatotropin to assume a native conformation. Somatotropin must be in a naturing environment to achieve the proper state of oxidation and conformation necessary for bioactivity. Because of the naturing-type of environment the solubilized refractile bodies gradually fold and form the desired end-product of properly natured monomer. This is in stark contrast to prior art methods using denaturants, which then require renaturation steps.

Figure 2:
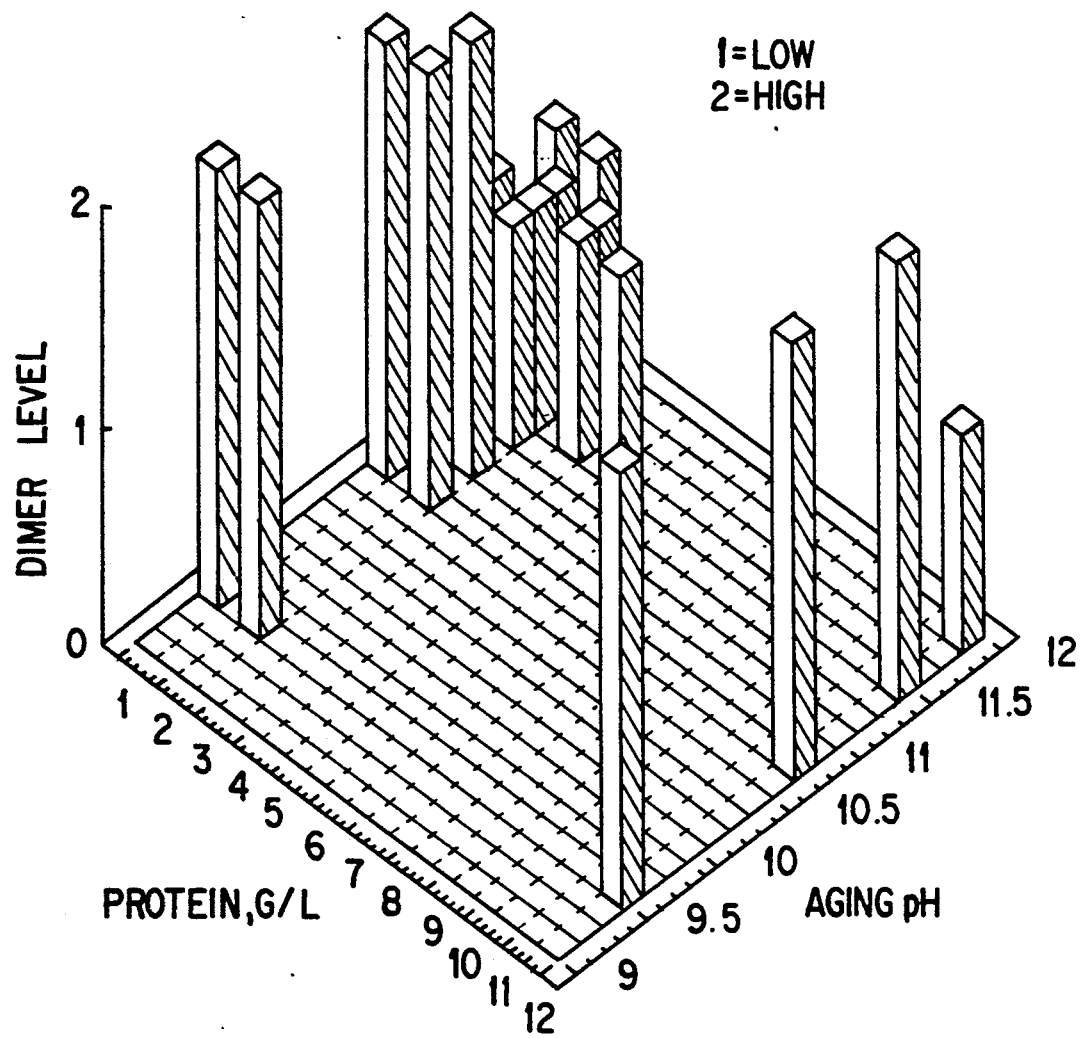
FIG. 2 diagramatically represents the amount of dimer formed as dependent upon aging pH and concentration of protein.

After the somatotropin refractile bodies are dissolved, the pH may be readjusted to a range from about pH 11 to about pH 12. Lowering the pH increases the rate of naturation. The pH can be lowered by any method, for example the addition of phosphoric acid. The readjusted range is preferably about pH 11.3 to pH 11.7 for minimization of dimer. Especially preferred is a pH of 11.5. Surprisingly, it is found that when the pH is lowered to the preferred range, less dimer and a greater amount of monomer is formed. The formation of less dimer and greater monomer by readjusting the pH is surprising because the percentage of dimer or monomer formed would be expected to remain the same. FIG. 2 shows the unexpected result that dimer formation is lessened using the preferred pH range of the present invention.

A pH lower than about pH 11 can be used, however, the yield is generally adversely affected and greater dimer formed. Additionally if the pH is lowered too far there is a risk that the somatotropin will precipitate from solution. Conversely, if the pH is not readjusted, the naturation process takes longer and degradation reactions such as deamidation are possible. However, different types of somatotropin (e.g. different analogs, derivatives, precursors or variants of growth hormone) may suggest varying the pH range and such variations are considered to be within the scope of the present invention.

The solution is maintained at the readjusted pH range for about 5 to about 12 hours (preferably about 10) at about 20° C.–30° C. until the monomer has reached its maximum. This is determined by gel permeation chromatography. FIGS. 3–7 show the evolution over time of the protein using the method of the present invention. Notice that FIGS. 3–7 show that the path is from higher molecular weight protein aggregates toward monomer instead of the conventionally proposed model using denaturants which would show monomer immediately formed and no change (or an increase) in molecular weight as the monomer correctly folded or joined with other protein molecules.

Figure 3:
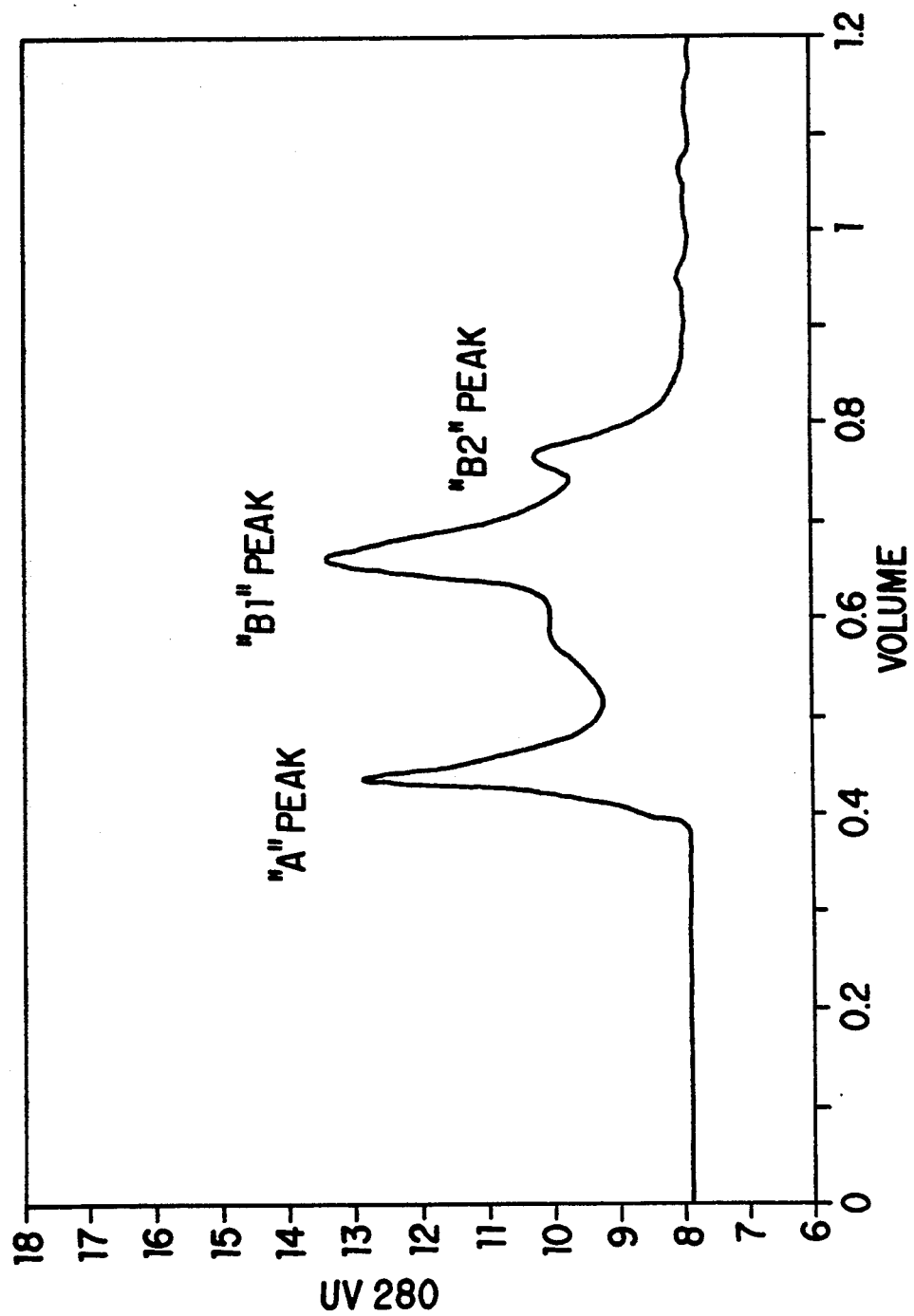
FIGS. 3-7 show the gel permeation chromatography results of the novel method over time (5 minutes, 1 hour, 2 hours, 5 hours and 10 hours, respectively).

FIG. 3 shows the results of gel permeation chromatography (gpc) after 5 minutes. Three peaks can be identified: the "A" peak at about 0.45 volume units on the abscissa the "B1" peak at about 0.65 units; and the "B2" peak at about 0.77 units. The "A" peak is comprised of proteinaceous impurities with molecular weights of over 1,000,000 daltons. The "B1" peak is aggregated somatotropin along with some proteinaceous impurities, e.g. E. coli host contaminants. The "B2" peak is the monomeric somatotropin (the "B2" peak may also have some remaining impurities as well as monomer).

Figure 4:
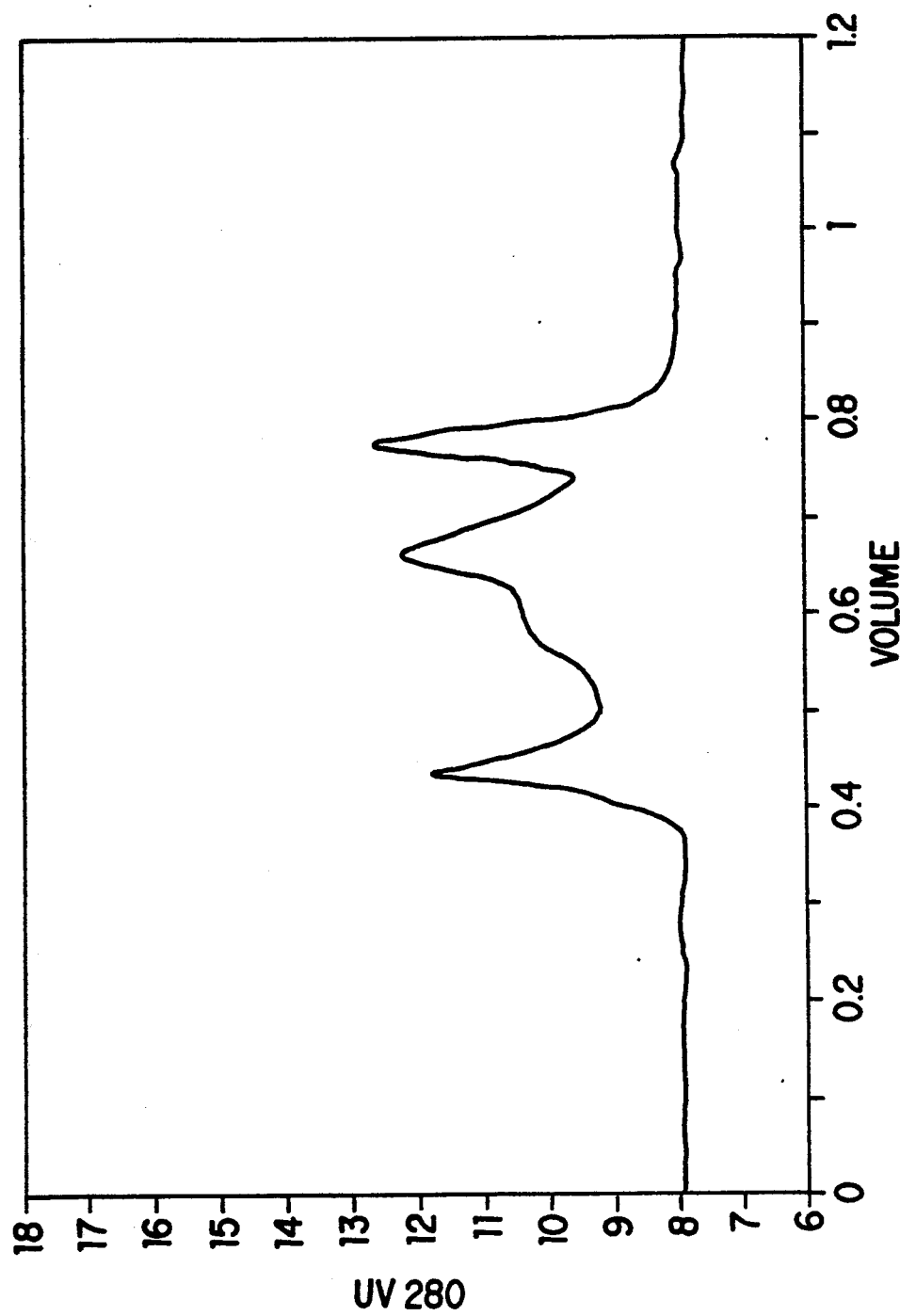

FIG. 4 shows the results of gpc after 1 hour. Both the "A" peak and the "B1" peak have diminished in size and the "B2" peak is markedly more pronounced.

Figure 5:
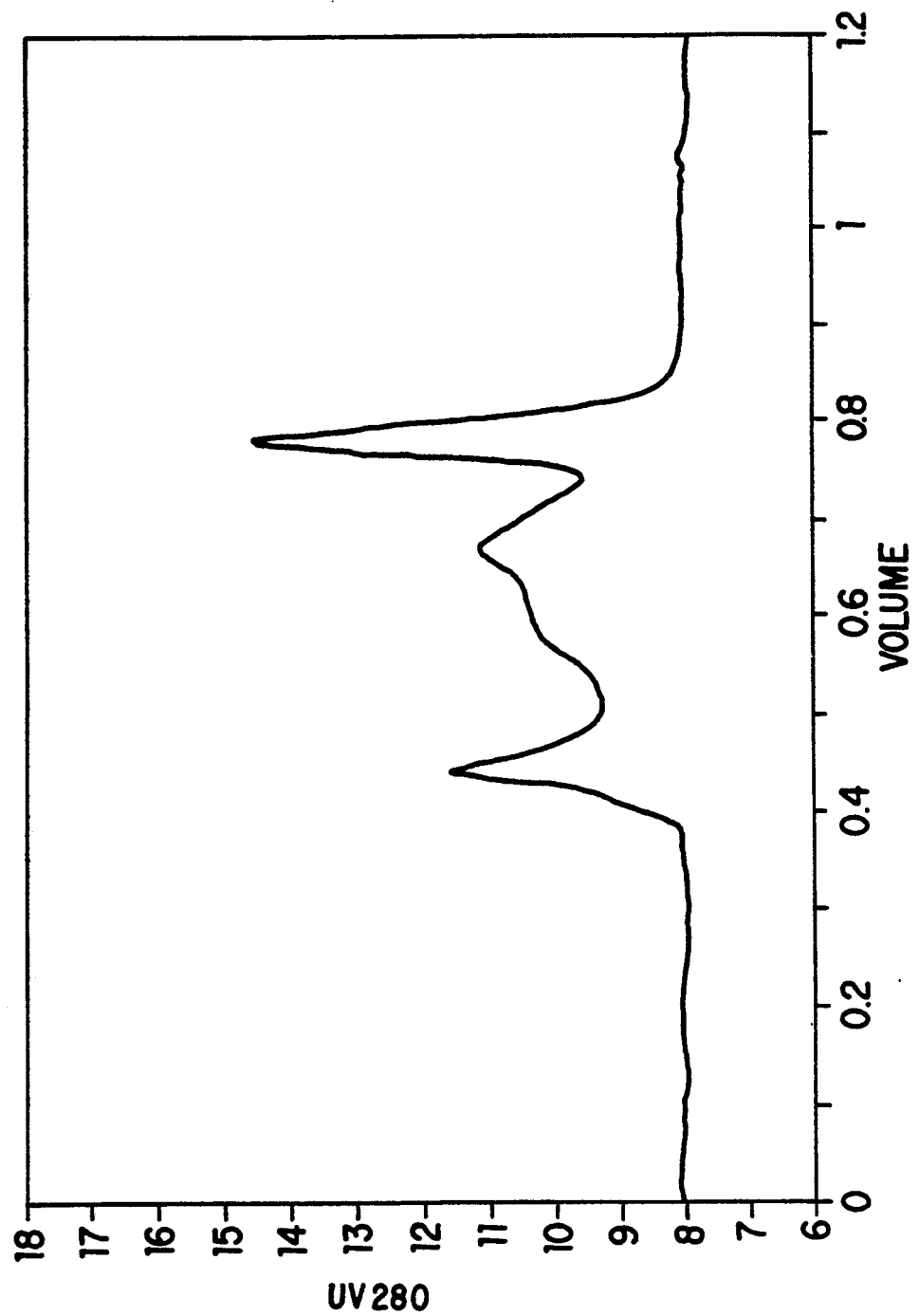

FIG. 5 shows the results of gpc after 2 hours. The "A" peak and the "B1" peak have further diminished in size and the "B2" peak has again increased.

Figure 6:
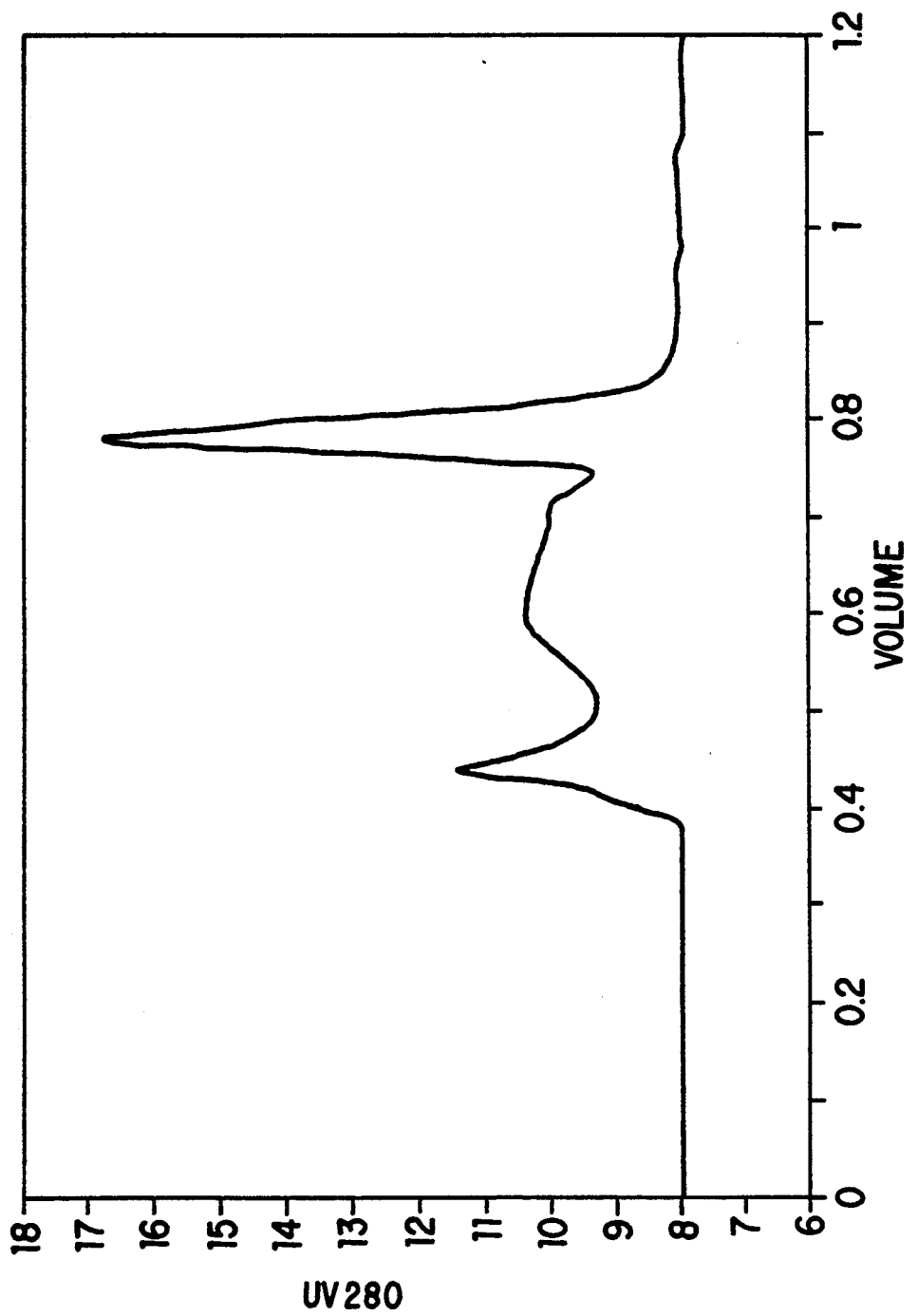

FIG. 6 shows the results of gpc after 5 hours. Notice that a small fourth peak or shoulder at about 0.7 volume units has appeared. This shoulder represents dimer formed. The shoulder in FIG. 6 shows the low dimer formation of the present novel method. In methods wherein high amounts of dimer are formed, an actual distinct peak is quite evident.

Figure 7:
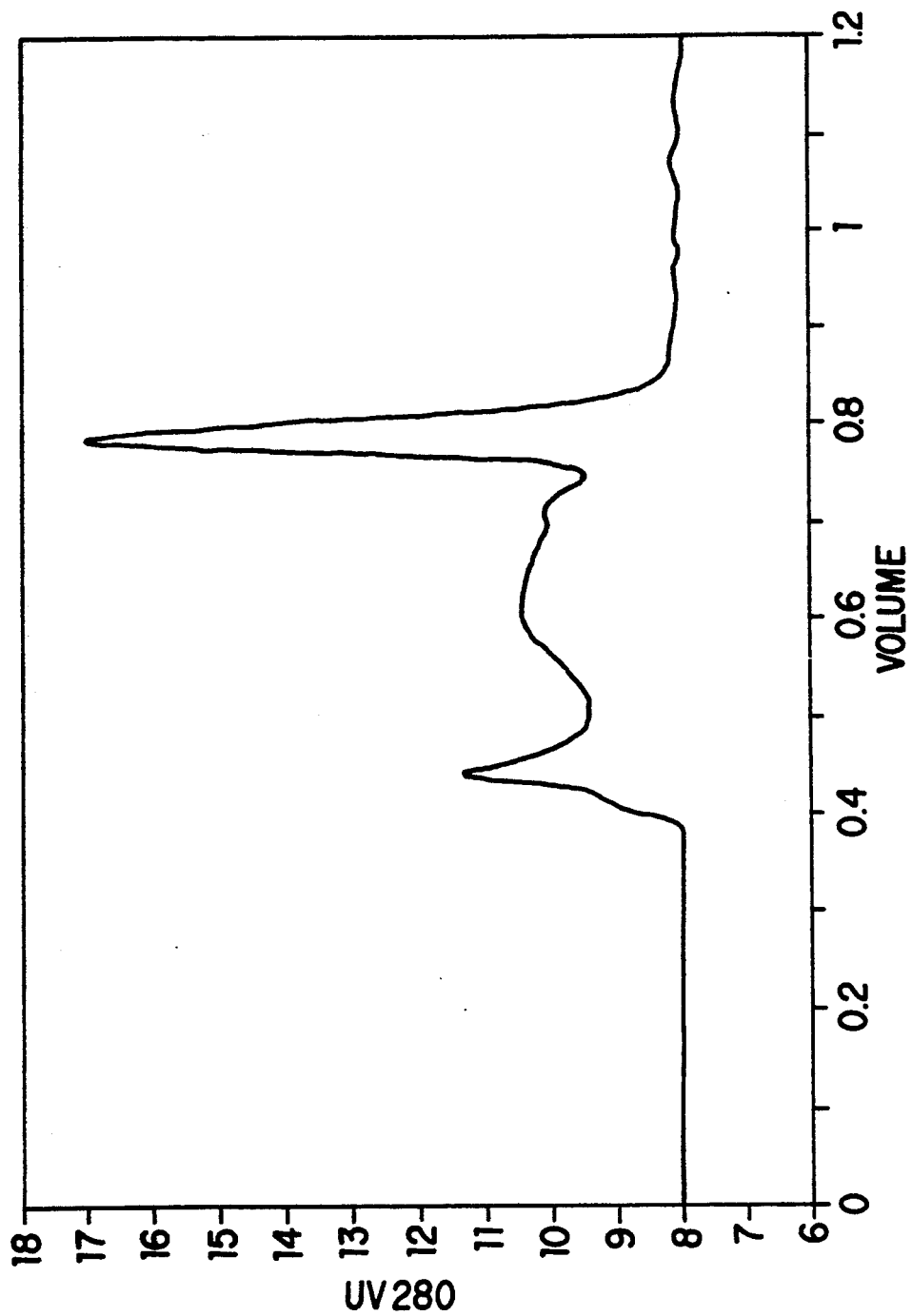

FIG. 7 shows the results of gpc after 10 hours. There is little change from FIG. 6, but the "B2" peak representing monomer has increased slightly.

FIGS. 3–7 show that the present invention creates a naturing environment. The protein molecules in the refractile bodies disentangle and are allowed to correctly fold to form the biologically active monomeric somatotropin without the use of any denaturants and without any separate renaturation steps or agents.

The resulting solution is comprised of properly natured monomeric somatotropin in a good yield. A good yield is about 30% to about 45% or higher of the total protein dissolved. Total protein includes all forms of somatotropin as well as all other non-somatotropin protein impurities such as E. coli host contaminants. Yields calculated on a somatotropin only basis would be much higher. Yields for methods employing chaotropic agents are about the same. Because the present invention uses no chaotropic agents, however, the resulting monomeric somatotropin has no traces of undesirable contaminating agents such as SDS, guanadine hydrochloride, or urea. The invention is further illustrated in the following non-limiting examples.

EXAMPLE 1

Bovine Somatotropin

Fermentation mash containing E. coli cells which have been genetically modified to produce bovine somatotropin inclusion bodies is centrifuged to separate the cells from the broth. The cells are reslurried and disrupted using two passes at 8000 psig through a Gaulin homogenizer. The suspension is centrifuged and the pellet reslurried and treated with lysozyme and Triton ® X-100 detergent at 37° C. The suspension is centrifuged and the pellet is washed twice with water and is centrifuged after each wash. The resulting pellet, containing the insoluble denatured bovine somatotropin, is added to water and adjusted to pH 12.15 with NaOH to bring the total protein concentration to approximately 2.5 g/l. After 20 minutes at pH 12.15 and 25° C., the clear solution is adjusted to pH 11.5 and is held for 8 hours. The solution is ultrafiltered on an Amicon ® H1P100-43 100K dalton cut-off hollow-fiber cartridge. The permeate is collected and concentrated using an Amicon ® H1P10-43 10K dalton cut-off hollow-fiber cartridge to approximately 5 g/L. The concentrated solution is adjusted to pH 9 using 1N HCl and applied at 20 g bST per L resin to a DEAE-Sepharose Fast Flow ® anion-exchanger which had been equilibrated with 10 mM borate, pH 9. After washing with the equilibration buffer, the bST is eluted using a 100 mM NaCl, 10 mM borate solution, at pH 9. The bST peak is concentrated and desalted with a dilute ammonia solution using an Amicon ® H1P10-43 hollow-fiber cartridge until the conductivity of the permeate is 100 microsiemens/cm. The desalted solution at approximately 2 g/L is lyophilized to yield bovine somatotropin which passes established biological and chemical tests.

EXAMPLE 2

Porcine Somatotropin

Fermentation mash containing *E. coli* cells which have been genetically modified to produce porcine somatotropin inclusion bodies is centrifuged to separate the cells from the broth. The cells are reslurried and disrupted using two passes at 8000 psig through a Gaulin homogenizer. The suspension is centrifuged and the pellet reslurried and treated with lysozyme and Triton ® X-100 detergent at 37° C. The suspension is centrifuged and the pellet is washed twice with water and is centrifuged after each wash. The resulting pellet, containing the insoluble porcine somatotropin is added to deionized water such that the total protein concentration is approximately 2.5 g/L. The resulting slurry is mixed well while adding 5N NaOH to raise the pH to 12.2. The solution clears slowly over five minutes. The solution is aged for 20 minutes at 20° C. The pH is then lowered to 11.5 using 1M $H_3PO_4$ and is aged for ten hours. The monomer concentration as measured by gel permeation chromatography is 1.05 g/L at the end of the aging period.

It is understood that many changes can be made to the present invention by one of ordinary skill in the art without departing from the spirit and scope of the present invention as defined in the following claims.

What is claimed is:

1. A method for solubilization and naturation of recombinantly derived somatotropin which comprises:
    (a) dispersing somatotropin refractile bodies into water in concentration of about 5 g/l;
    (b) adjusting the pH to range from pH 11.5 to pH 12.5;
    (c) maintaining the pH range for about two minutes to twenty minutes to solubilize the refractile bodies;
    (d) readjusting the pH of the solution to a range from 11 to 12; and
    (e) maintaining the solution at the readjusted pH range for about five hours to twelve hours to effect naturation of the somatotropin, and wherein all steps of the process are carried out in the absence of chaotropic and denaturing agents.

2. The method as in claim 1 wherein the somatotropin is bovine or porcine somatotropin.

3. The method as claimed in claim 1 wherein the pH in step (b) is adjusted to a range from about pH 12.0 to pH 12.2 and the pH range is readjusted in step (d) to about pH 11.3 to pH 11.7.

4. The method as in claim 2 wherein the concentration in step (a) is about 0.5 g/l to 5 g/l.

5. The method as in claim 4 wherein the concentration in step (a) is about 2.5 g/l, the pH is readjusted in step (d) to pH 11.5 and the time in step (e) is about 10 hours.

6. A method for solubilization and naturation of somatotropin which comprises:
    (a) dispersing somatotropin refractile bodies into water in concentration of less than about 5 g/l;
    (b) adjusting the pH to a range from pH 11.5 to pH 12.5; and
    (c) maintaining the pH range for about two minutes to twenty minutes to effect naturation of the somatotropin, and wherein all steps of the process are carried out in the absence of chaotropic and denaturing agents.

7. The method in claim 6 wherein the pH is about pH 12.0 to about pH 12.2, the concentration is about 0.5 g/l to about 5 g/l, and the time is about 5 hours to about 12 hours at a temperature of about 20° C. to about 30° C.

* * * * *